United States Patent [19]

Schrack

[11] Patent Number: 4,768,231
[45] Date of Patent: Sep. 6, 1988

[54] PROTECTIVE HEADGEAR

[76] Inventor: Michael E. Schrack, 4435 Portola Dr., Santa Cruz, Calif. 95062

[21] Appl. No.: 55,983

[22] Filed: Jun. 1, 1987

[51] Int. Cl.⁴ .......................... A42B 1/12; A42B 1/18; A42B 1/24
[52] U.S. Cl. .............................. 2/12; 2/68; 2/13; 2/197; 351/158
[58] Field of Search .................. 2/12, 13, 68, 197, 177, 2/195, 200; 351/123, 155, 158

[56] References Cited

U.S. PATENT DOCUMENTS

| | | | |
|---|---|---|---|
| 1,666,098 | 4/1928 | Kaul | 2/68 |
| 2,580,744 | 1/1952 | Edsall | 2/13 |
| 2,869,137 | 1/1959 | Scherz | 2/197 |
| 2,891,251 | 6/1959 | Ebersole | 2/13 |
| 3,108,283 | 10/1963 | Gasaway | 2/68 |
| 4,096,589 | 6/1978 | Goldstein | 2/12 |
| 4,549,793 | 10/1985 | Yoon | 351/123 X |
| 4,612,672 | 9/1986 | Schrack | 2/68 |

OTHER PUBLICATIONS

Gershman, "Self Adhering Nylon Tapes", 10-18-58, J.A.M.A., vol. 68, No. 7, p. 930.

Primary Examiner—Peter Nerbun
Attorney, Agent, or Firm—Fliesler, Dubb, Meyer & Lovejoy

[57] ABSTRACT

A water sports headgear of high durability and buoyancy being stretchably retained on the wearer's head. A visor of a closed-cell foam type material is provided for protection from the sun. The visor is attached to the lower front of a head-surrounding strap of the same material. Curvatures of reduced foam in the strap above the ear area are provided to allow the headgear to fit snugly and at a lower level on the user's head. A Velcro sandwich-type adjusting system connects the ends of the strap at the rear of the user's head. Velcro tabs adhered to the lower temple area of the circumference strap are provided to secure sunglasses. The foam visor and strap parts are dipped in or sprayed with a liquid vinyl-type material creating a stretchable, water-impervious covering.

2 Claims, 3 Drawing Sheets

PROTECTIVE HEADGEAR

BACKGROUND OF THE INVENTION

1. Field of the Invention

The present invention relates to protective headgear in general and in particular to buoyant, lightweight, snug-fitting sports headgear for water activities.

2. Description of the Prior Art

In many water sports, such as surfing, windsurfing, sailing, river rafting, kyaking, jet skiing, waterskiing and the like, protective headgear is desirable to protect the eyes of the user from the elements. For example, many water sports enthusiasts use a cap, visor, and/or sunglasses to protect their eyes and face from the direct rays of the sun which frequently cause such conditions as sun stroke or pteryguim of the eye.

Unfortunately, prolonged salt water and sun absorption can rapidly deteriorate many forms of caps and visors. Also, retrieving sunglasses or headgear which are easily dislodged by wave, wind or turbulence from rapids can be a problem.

Head gear which is designed specifically for a particular sport is available; some with hard shells, some lined with thick foam, and others made of thin rubber. Each of them may work well for its particular sport, but often they are rejected by the general public as being too awkward, bulky, or heavy.

While a more acceptable and functional headgear for water sports of the floatable, lightweight and snug-fitting variety specifically for use in highly active water sports, such as surfing, is described in U.S. Pat. No. 4,612,672, issued to applicant on Sept. 23, 1986, the present invention relates to a simplified, more casual form of headgear which is intended to benefit a much broader range of water sport enthusiasts.

SUMMARY OF THE INVENTION

In view of the foregoing, a principal object of the present invention is a water impervious headgear which is suitable for all types of water sports.

In accordance with the above object, there is provided a protective headgear which offers a broad range of use. High buoyancy, water resistance and comfort are desired features of such a headgear. Direct sun and glare reduction are also desirable.

In an embodiment of the invention there is provided a closed-cell foam strap adapted to surround a wearer's head. A curvature in the bottom edge of the strap in the brow area, and a curvature as well as reduced foam over the ear areas of the strap allows the strap to fit lower on the brow and rear of the head. By adding a downward curvature near the temples, the visor, as well as sunglass attachment tabs, can be more suitably placed for achieving their desired functions. Combined curvatures allow more surface area of this strap to achieve a snug grip, lower on the head. Preferably, the strap and visor are cut from a closed-cell foam type sheet material of approximately ¼-inch thick.

The ends of the strap are joined together at the rear of the head by Velcro adjustment pieces which have been fixed to the ends of the strap.

The visor and strap and then dipped or sprayed with a soft, stretchable water-impervious covering. The cover and foam in combination provide a headgear which is very buoyant in water for extended periods.

In an alternative embodiment of this invention, a cap of material may partially or fully enclose the top portion of the strap to minimize direct sun contact. Also, the strap may be of various lengths or adjustable to accommodate all wearers' heads.

BRIEF DESCRIPTION OF THE DRAWINGS

Other objects, features and advantages of the present invention will become apparent upon consideration of the following detailed description and the accompany drawings, in which.

DESCRIPTION OF THE PREFERRED EMBODIMENTS

Figure 2:
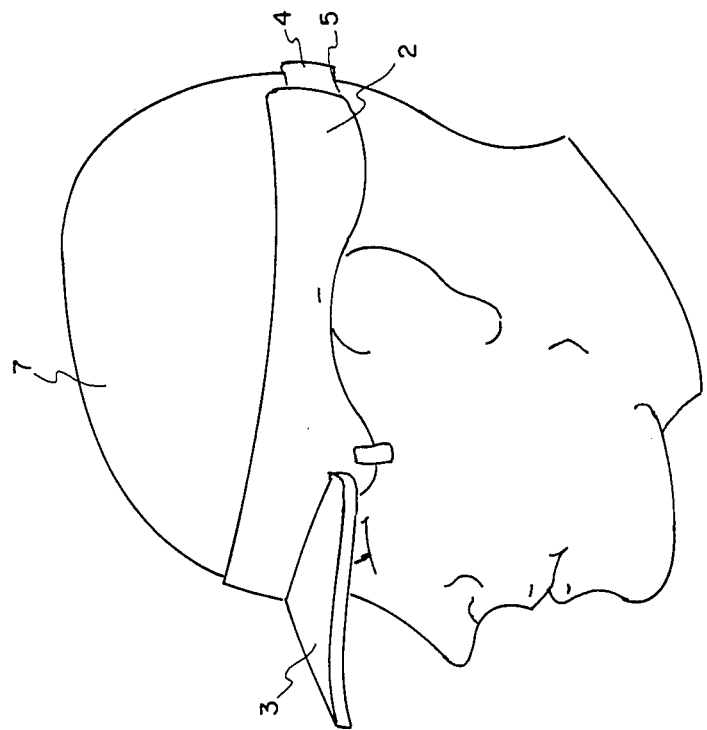
FIG. 2 illustrates a side view of the embodiment of FIG. 1 on a wearer's head.
Figure 1:
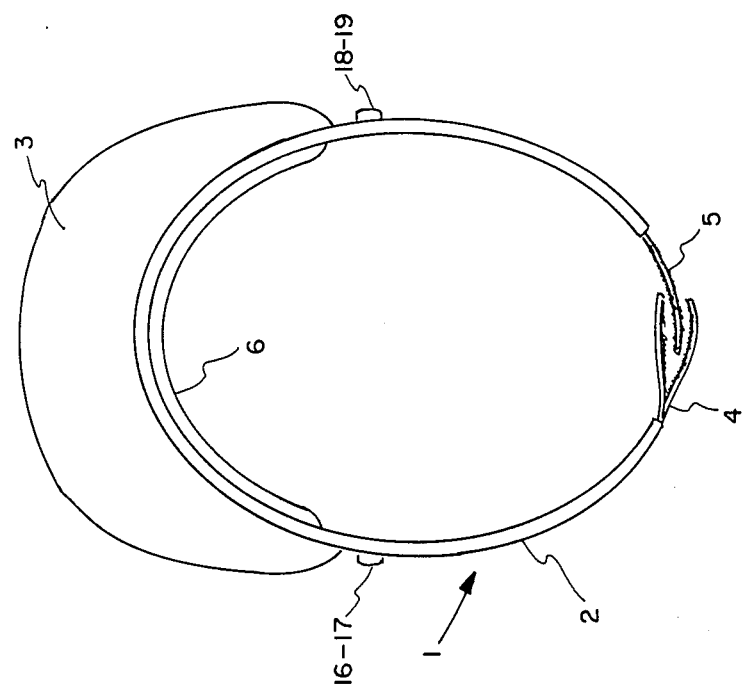
FIG. 1 is a top plan view of an embodiment of the present invention.

Referring to FIGS. 1 and 2, there is provided in accordance with the present invention a headgear especially designed for use in water sports designated generally as 1. In the headgear 1 there is provided a head strap member 2, a visor 3, rear hook and loop adjusting strips 4 and 5, a forehead sweat band 6, and sunglass attachment tabs 16-19. The hook and loop material is of the type having the brand name VELCRO.

Referring to FIG. 2, the strap member 2, visor 3 and adjusting strips 4 and 5 are shown in their snug, low-fitting position as they are stretched to surround a user's head 7, at a level just above the wearer's ears and eyes.

Figure 5:
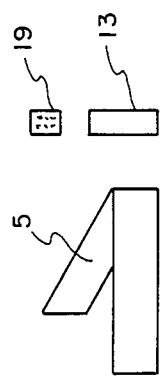
FIG. 5 is a plan view of the right side sunglass attachment tabs and right rear adjusting strap of FIG. 1, prior to assembly.
Figure 4:
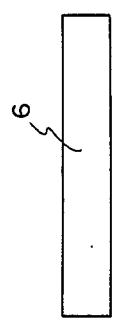
FIG. 4 is a plan view of a sweat band in the embodiment of FIG. 1, prior to assembly.
Figure 3:
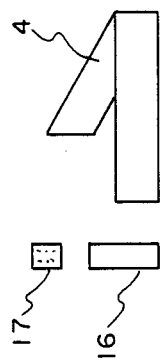
FIG. 3 is a plan view of the left side sunglass attachment tabs and left rear adjusting strap of FIG. 1, prior to assembly.

Referring to FIGS. 3-5, the hook and loop components 16, 17, 4, 6, 5, 18, and 19 of FIG. 1 are shown prior to assembly.

Figure 6:
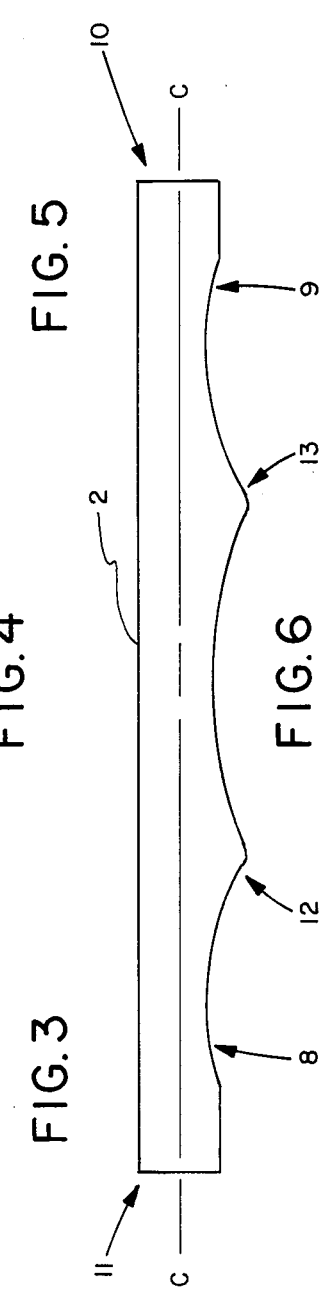
FIG. 6 is a plan view of a head strap member in the embodiment of FIG. 1, prior to assembly.

Referring to FIG. 6, strap member 2 is provided with various curvatures, each with the desired function of retaining the headgear 1 at a lower and more secured level on the wearer's head. This lowering is achieved by removing areas 8 and 9 from the bottom edge of member 2 as well as curving the top line of member 2 downwardly toward the ends 10 and 11. Added downwardly directed curvatures 12 and 13 of member 2 allow the visor 3 to be comfortably worn at a lower brow level than is usually possible with similar prior known headgear, as illustrated in FIG. 2.

Figure 10:
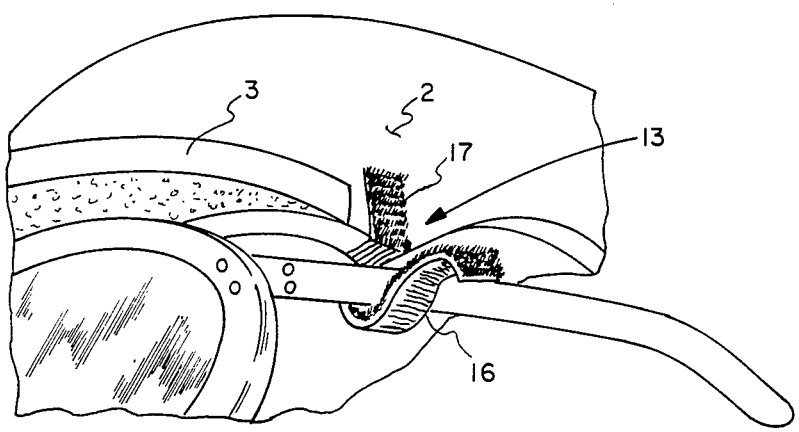
FIG. 10 is a perspective view showing one of the sunglass attachment tabs of the present invention.

The hook and loop fastening tabs 16-17 and 18-19 are fixed to curvature ends 12 and 13, as shown more clearly in FIG. 10, for the purpose of securing prescription glasses or sunglasses to headgear 1, enabling the glasses to remain afloat for easy retrieval in the event the headgear is knocked off a user's head and into water.

Strap member 2 and visor 3 are preferably cut or dye-stamped from approximately ¼-thick sheets of soft, resilient, closed-cell foam type material.

Figure 7:
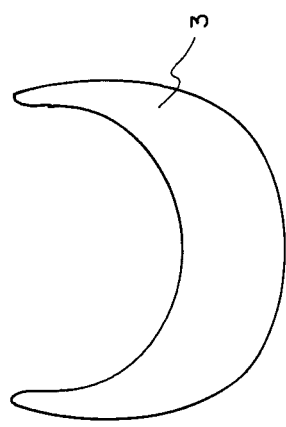
FIG. 7 is a plan view of the visor of FIG. 1, prior to assembly.

Referring to FIG. 7, the brim or visor 3 is shown prior to assembly.

Figure 8:
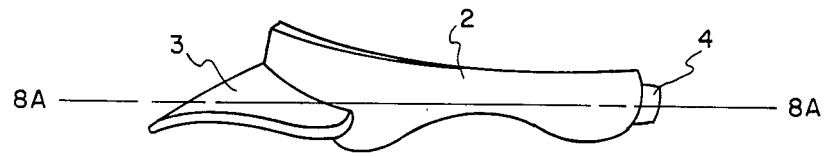
FIG. 8 is a side view of FIG. 1 with a line 8A—8A representing the surface of water for illustrating the highly buoyant character of the present invention.

Referring to FIG. 8, the aforementioned strap member 2 and visor 3 are fixed together and provided with a soft, flexible vinyl-type dip or spray which bonds to the foam, creating a slightly stretchable water impervious soft shell or cover. The resulting durable, non-deflatable and highly buoyant material will remain afloat, high on the surface of the water for extended periods of time. Line 8A—8A of FIG. 8 represents a typical water line illustrating the buoyancy of headgear 1 in water.

Figure 9:
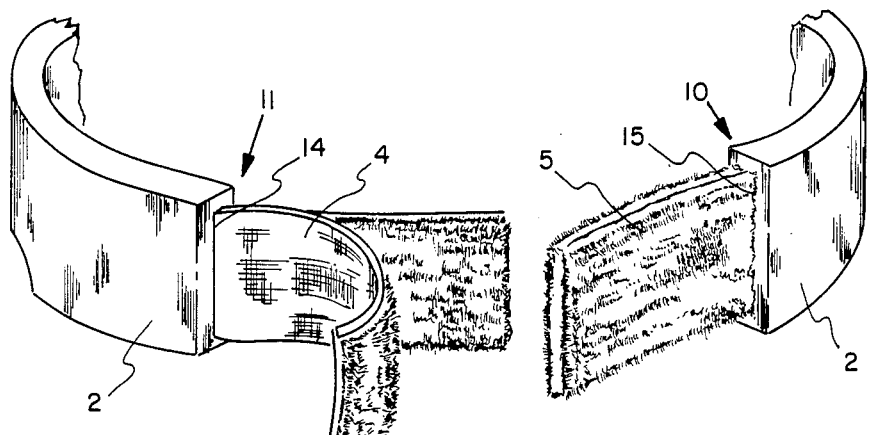
FIG. 9 illustrates an enlarged partial rear view of the strap member of FIG. 1, detailing the adjusting system.

Referring to FIG. 9, a sectional view of FIG. 1 detailing the rear hook and loop adjusting system is illustrated. An approximately 6-inch strip of hook material 4 is folded in half and the resulting fold section 14 is fixed to the end 11 of member 2. An adjacent identical 6-inch strip of loop material 5 is folded and the halves are joined together by ultrasonic weld, sewing or adhesives. The end 15 is fixed to end 10 of member 2. By inserting strip 5 between strips 4 and applying pressure, an overlap lock system of adjustment is achieved.

While an embodiment of the present invention is described above, it is contemplated that various modifications may be made thereto without departing from the spirit and scope thereof. For example, a cap of material may be provided to enclose or partially enclose the top portion of strap 2. A wide range of sizes, various colors and other types of decorative features may be used for distinguishing contestants, for instance, and increasing visibility of the headgear 1. Sweat band 6 may be removable by use of self-adhesive type materials such as the hook and loop material available through Velcro U.S.A. Inc., located at 4115 San Fernando Road, P.O. Box 6276, Glendale, Calif. Moreover, while described for use in water sports, it will be appreciated that headgear 1 may be used and provide shade, durability and retainment during other types of sports activities such as skiing or the like. Accordingly, it is intended that the embodiment described be considered only as an illustration of the present invention and that the scope thereof should not be limited thereto but be determined by reference to the claims hereinafter provided.

What is claimed is:

1. A highly buoyant, lightweight, durable, snug-fitting, water impervious headgear comprising:

a head strap member having a centerline which extends between a first and a second end thereof for fitting about a user's head, said strap member having a lower edge which is provided with a first and a second curved portion which extend inwardly toward said centerline above a user's right and left ears, respectively, a third curved portion which extends inwardly toward said centerline in the area of a user's forehead between the user's right and left temple and a fourth and fifth curved portion which extends outwardly from said centerline in the vicinity of said user's right and left temples, respectively;

means fixed to said fourth and fifth curved portions for releasably attaching the right and left bows of a pair of eye glasses, respectively, to said strap member;

means located at opposite ends of said head strap member for adjustably connecting said ends to each other; and a sun visor which is fixed to said head strap member along a line substantially parallel to the line of curvature of said third curved portion.

2. A highly buoyant, lightweight, durable, snug-fitting, water impervious headgear comprising:

a head strap member having a centerline which extends between a first and a second end thereof for fitting about a user's head, said strap member having a lower edge which is provided with a first and a second curved portion which extend inwardly toward said centerline above a user's right and left ears, respectively, a third curved portion which extends inwardly toward said centerline in the area of a user's forehead between the user's right and left temple and a fourth and fifth curved portion which extends outwardly from said centerline in the vicinity of said user's right and left temples, respectively; and a sun visor which is fixed to said head strap member along a line substantially parallel to the line of curvature of said third curved portion, said head strap and said sun visor comprising a sheet of closed-cell foam material which is entirely enclosed within a water-impervious coating;

means fixed to said fourth and fifth curved portions for releasably attaching the right and left bows of a pair of eye glasses, respectively, to said strap member; and means located at opposite ends of said head strap member for adjustably connecting said ends to each other.

* * * * *